United States Patent [19]

Gateau et al.

[11] Patent Number: 5,735,915
[45] Date of Patent: Apr. 7, 1998

[54] SIMPLIFIED PROCESS FOR PRODUCTION OF ALKENYLSUCCINIMIDES OR POLYALKENYLSUCCINIMIDES

[75] Inventors: Patrick Gateau, Maurepas; Daniel Binet, Rueil Malmaison; Fabrice Paille, Saint Maur des Fosses; Jean-Pierre Durand, Chatou, all of France

[73] Assignee: Institut Francais du Petrole, Rueil-Malmaison, France

[21] Appl. No.: 784,382

[22] Filed: Jan. 17, 1997

[30] Foreign Application Priority Data

Jan. 18, 1996 [FR] France ................... 96 00645

[51] Int. Cl.⁶ ..................... C10L 1/22; C10M 133/16
[52] U.S. Cl. ................ 44/347; 508/293; 508/292; 558/546
[58] Field of Search ................ 508/293, 292; 44/347; 548/546

[56] References Cited

U.S. PATENT DOCUMENTS

| | | |
|---|---|---|
| 3,914,203 | 10/1975 | Lee .......................... 260/78.4 |
| 4,081,388 | 3/1978 | Soula ......................... 548/546 |
| 4,086,251 | 4/1978 | Cengel et al. . |
| 4,234,435 | 11/1980 | Meinhardt et al. .............. 252/51.5 |
| 4,235,786 | 11/1980 | Wisotsky . |
| 4,278,604 | 7/1981 | Powell . |
| 4,482,464 | 11/1984 | Karol et al. ................... 508/291 |
| 4,496,746 | 1/1985 | Powell . |
| 4,604,221 | 8/1986 | Bryant . |
| 4,670,516 | 6/1987 | Sackmann et al. . |
| 4,997,456 | 3/1991 | Malfer . |
| 5,122,616 | 6/1992 | Malfer ......................... 548/546 |

FOREIGN PATENT DOCUMENTS

| | | |
|---|---|---|
| 0 545 653 | 6/1993 | European Pat. Off. . |
| 0 684 262 | 11/1995 | European Pat. Off. . |
| 922878 | 4/1963 | United Kingdom . |
| 2 231 873 | 11/1990 | United Kingdom . |
| 94/13718 | 6/1994 | WIPO . |

*Primary Examiner*—Margaret Medley
*Attorney, Agent, or Firm*—Millen, White, Zelane, & Branigan, P.C.

[57] ABSTRACT

A simplified process for preparation of an alkenylsuccinimide or a polyalkenylsuccinimide is described, characterized in that it comprises successively: a stage (a) in which an alkenylsuccinic anhydride or a polyalkenylsuccinic anhydride is prepared by bringing about an ene-synthesis reaction between at least one olefin or one polyolefin and at least one unsaturated dicarboxylic anhydride that is selected from maleic anhydride and the maleic anhydrides that are substituted by 1 or 2 methyl groups, characterized in that said reaction is carried out within at least one aromatic solvent that is selected from toluene and the xylenes that are used at a ratio of between 30 to 70% by weight of the reaction mixture and in which a fraction of said unsaturated dicarboxylic anhydride does not react with said olefin or polyolefin; a stage (b) in which the product of stage (a) that contains unsaturated, unreacted dicarboxylic anhydride is reacted with at least one alcohol or an amine; and a stage (c) in which the product that is obtained in stage (b) is reacted with an amine.

These succinimides can be used as detergent additives for engine fuels and as ashless dispersing additives for engine lubricants.

18 Claims, No Drawings

SIMPLIFIED PROCESS FOR PRODUCTION OF ALKENYLSUCCINIMIDES OR POLYALKENYLSUCCINIMIDES

This invention relates to a simplified process for production of alkenylsuccinimides or polyalkenylsuccinimides that are free of chlorine.

In the field of additives for petroleum products, particularly detergent additives for engine fuels and dispersants for engine lubricants, functionalized polyisobutenes are often used, most often with maleic anhydride, to synthesize the amphiphilic compounds that are desirable in these applications. The polyisobutenylsuccinic anhydrides under consideration are prepared according to two main processes.

The first consists of the condensation of maleic anhydride on polyisobutene following an ene-synthesis reaction. This reaction requires a high temperature and reaction times such that, under the conditions, resins appear that result from the polymerization of maleic anhydride. These secondary products require a filtration stage, which is made more difficult by the consistency of these products. Improvements aiming at reducing the mount of resins have been proposed. They consist most often in carrying out the reaction in the presence of radical-like polymerization inhibitors, as in documents DE-A-1 102 142, DE-A-3 320 468 and U.S. Pat. No. 3,476,774; halogenated compounds as in documents GB-A-1 356 802, GB-A-1 480 453 (=FR-A-2 273 014), U.S. Pat. No. 3,960,900, DE-A-3 320 468 already cited, U.S. Pat. No. 4,278,604, and U.S. Pat. No. 4,255,340; metallic salts, as in documents. GB-A-2 081 274 and WO-A-082/00467; or peroxides as in document U.S. Pat. No. 4,599,432 (-FR-A-2 555 595). Another method, which is described in, for example, document U.S. Pat. No. 4,496,746, consists in reacting maleic anhydride in emulsion in an inert solvent, thanks to the use of a surfactant. In neither case are the secondary products ever totally eliminated.

In a second type of process, first chlorination of polyisobutene is carried out, followed by condensation of the chlorinated polyisobutene and maleic anhydride. This process is competitive with the preceding one thanks to the reduced reaction temperature, better conversion, and the absence of secondary reactions that lead to insoluble resins. This process usually leads, however, to products that contain a certain amount of residual chlorine, which excludes them from an increasingly large number of applications, in view of the increasingly strict specifications regarding chlorine contents of additives for petroleum products.

These polyisobutenylsuccinic anhydrides are then modified most often with amines and should therefore be freed of any trace of free maleic anhydride. To do this, an evaporation stage under vacuum is necessary.

This invention proposes a simplified process for production of alkenylsuccinimides or polyalkenylsuccinimides that are free of chlorine, which do not involve an emulsion reaction or a suspension reaction and in which the secondary products are totally eliminated; this avoids a long, difficult, and expensive filtration stage. Further, the process that is described in this invention does not require the elimination of the unreacted maleic anhydride for the preparation of additives for petroleum products that are free of chlorine, particularly detergent additives for engine fuels.

The process that is described in this invention comprises a stage of production of alkenylsuccinic anhydrides or polyalkenylsuccinic anhydrides by reaction between an olefin or a polyolefin and an unsaturated dicarboxylic anhydride, under conditions of ene-synthesis and in solution in at least one aromatic solvent that is selected from toluene and the xylenes, used at a ratio between 30 and 70% by weight of the reaction mixture.

The olefins and polyolefins that are used can have an average molecular weight at a number of between 400 and 10,000 and preferably between 400 and 3,000. The polyolefins under consideration consist more particularly of polyisobutenes that have a content of "exo" double bonds that is greater than 50%. They are preferably obtained by polymerization of the isobutene in the presence of a catalyst that does not contain chlorine, such as, for example, boron trifluoride. The unsaturated carboxylic anhydride is selected more particularly from the group that is formed by maleic anhydride and the maleic anhydrides that are substituted by one or two methyl groups on the carbon atoms of the ethylenic bond, namely citraconic (methylmaleic) anhydride and pyrocinchonic (dimethylmaleic) anhydride. Preferably, maleic anhydride is used.

One of the basic characteristics of the process of the invention is the implementation of the reaction of ene-synthesis within an aromatic solvent that is selected from toluene and xylenes, at a content of between 30 and 70% by weight, preferably 35 to 60% by weight and, for example, 50% by weight relative to the reaction mixture.

Further, the reaction is carried out at a temperature of between 150° and 300° C., preferably between 180° and 25° C., for example, under autogenous pressure. In general, the pressure that is developed during the reaction is between 2 and 40 bar, more particularly between 3 and 10 bar.

The maleic anhydride or substituted maleic anhydride is in general used at a molar ratio of 0.5 to 2, preferably 1 to 1.1, relative to the olefin or the polyolefin (most often polyisobutene).

The alkenylsuccinic anhydrides and polyalkenylsuccinic anhydrides (in particular polyisobutenylsuccinic anhydrides) are obtained by the process of the invention, with high yields, which can reach 85% and do not contain secondary products.

The process of this invention comprises a second stage that has as its object the avoidance of any purification of the product that is obtained during the first stage. The maleic anhydride that has not reacted during the ene-synthesis is modified by compounds such as alcohols or amines to solubilize it and to decrease its reactivity compared to amines that are used during the synthesis of detergent additives for engine fuels or ashless dispersing additives for engine lubricants.

The alcohols that are used are more particularly polypropylene glycols, copolymers of ethylene oxide and propylene oxide or polypropylene glycol monoethers.

The amines that are used are polyoxyalkylene-amines, alkenylamines, or else polyalkenylsuccinimides with a primary amine group.

The alcohols or the amines are introduced into the reaction mixture that is derived from the first stage of the process at a molar ratio of between 1 and 1.5 relative to the residual maleic anhydride that is present. The reaction is carried out at a temperature between ambient temperature and the boiling point of the solvent.

In a third stage, the reaction mixture that is derived from the second stage of the process is modified in a known way, by reaction with amines to form imides.

The amines that are used in this stage are more particularly polyethylene-polyamines such as triethylenetetramine or tetraethylenepentamine that are used, for example, at a molar ratio of 0.5 to 1 relative to the alkenylsuccinic anhydride or polyalkenylsuccinic anhydride (in particular polyisobutenylsuccinic anhydride). The reaction is generally carried out at the boiling point of the aromatic solvent that is used.

The products as obtained by the process described above also constitute an object of the invention. They can be used as detergent additives for fuels and, in this case, they can be used together with a carrying oil, such as a polypropylene glycol or a polypropylene glycol ether. They can also be used as ashless dispersing additives for engine lubricants.

The following examples illustrate the invention.

EXAMPLE 1

Introduced into an autoclave that is equipped with a stirring system are:

- 250 g of polyisobutene of average molecular weight at a number close to 1000 and whose composition of terminal double bonds, determined by NMR of the proton, is as follows:
  - 90% of "exo" double bonds;
  - 10% of "endo" double bonds;
- 24.5 g of maleic anhydride;
- and 147.8 g of xylenes, or 35% by weight of the reaction mixture.

The mixture is stripped by nitrogen scavenging at ambient temperature. It is then stirred for 15 hours at 200° C. The pressure that is developed during the reaction is 2.2 bar. No secondary product is formed. On a fraction of the reaction mixture, the solvent and the unreacted maleic anhydride are eliminated by distillation under vacuum. The anhydride index of the product that is obtained (number of moles of anhydride per 100 g of product) is 0.067. The concentration of free maleic anhydride in the reaction mixture is determined by steric exclusion chromatography. This concentration is 1.64% by weight.

71.7 g of a polypropylene glycol with a molecular weight that is close to 1000 and 38.6 g of xylenes are added to 400 g of the reaction mixture above while being stirred at ambient temperature. The solution is brought to reflux of the solvent for 3 hours.

After cooling, 12.4 g of xylenes and 23 g of tetraethylenepentamine are added while being stirred. The reaction mixture is brought to reflux of the solvent for 5 hours. About 3 cm$^3$ of water is eliminated. The solution that is obtained has a nitrogen content of 1.6% by weight.

EXAMPLE 2

The first stage of Example 1 is repeated by bringing the reaction temperature to 220° C. The pressure that is developed during the reaction is then 5 bar. The product that is obtained has an anhydride index of 0.075. The reaction solution contains 1.1% by weight of unreacted maleic anhydride.

The second and third stages of the process are carried out under conditions that are identical to those of Example 1, by adapting the amounts of polypropylene glycol and tetraethylenepentamine to the anhydride index of the product and to the free anhydride that is present. Thus, for 400 g of the reaction mixture, 48.3 g of polypropylene glycol and then 25.9 g of tetraethylenepentamine are added. The solution that is obtained has a nitrogen content of 1.9% by weight.

EXAMPLE 3

If, in Example 2, all other things being equal, the polypropylene glycol is replaced by 99.4 g of a solution that contains 70% by weight of a polyisobutenylmonosuccimide that is obtained by reaction between a polyisobutenylsuccinic anhydride with an anhydride index that is equal to 0.075 and a triethylenetetramine at an anhydride/polyethylene-amine molar ratio of 1, the solution that is obtained has a nitrogen content of 2.2% by weight.

EXAMPLE 4

If, in Example 1, all other things being equal, the polypropylene glycol is replaced by 14 g of polypropylene glycol diamine with an average molecular weight of close to 400, the solution that is obtained has a nitrogen content of 2.07% by weight.

EXAMPLE 5

(For Comparison)

If, in Example 1, all other things being equal, the reaction is carried out in the presence of 91.5 g of xylenes, or 25% by weight of reagents used, the formation of oily and brown secondary products is noted. The presence of these insoluble products precludes any use of the product without preliminary purification.

EXAMPLE 6

(For Comparison)

Introduced into an autoclave that is equipped with a stirring system are:

- 250 g of the polyisobutene of Example 1;
- 24.5 g of maleic anhydride;
- and 147.8 g of xylenes, or 35% by weight of the reaction mixture.

The mixture is stripped by nitrogen scavenging at ambient temperature. It is then stirred for 15 hours at 200° C. The product that is obtained has an anhydride index of 0.067.

12.4% xylenes and 23 g of tetraethylenepentamine are added to 400 g of the reaction mixture obtained at ambient temperature and while being stirred. The mixture is stirred for 5 hours with reflux of the solvent. After cooling, the presence of insoluble product is noted in the reaction medium, which precludes any use of the product. The amount of insoluble product that is present in the medium, evaluated by dilution with xylene, filtration and drying, is 0.65% by weight.

EXAMPLE 7

Test on a Diesel Engine

A test of the clogging of the injectors on an XUD9 engine is carried out. The fuel that is used is a gas oil whose characteristics are presented in detail in Table 1. The clogging tendency is derived from the average residual flow of four injectors, obtained after the engine has run for 6 hours. The tests are carried out compared to gas oil alone, by adding the latter with 500 ppm of the solutions that are obtained in Examples 1 and 2.

TABLE 1

| Density | 837.2 kg/m$^3$ |
|---|---|
| Sulfur content | 0.045% by weight |
| Distillation | |
| Initial point | 204.5° C. |
| 5% | 240.0° C. |
| 10% | 253.0° C. |
| 20% | 269.5° C. |
| 30% | 280.5° C. |

TABLE 1-continued

| 40% | 287.5° C. |
|---|---|
| 50% | 293.0° C. |
| 60% | 298.0° C. |
| 70% | 303.5° C. |
| 80% | 309.5° C. |
| 90% | 321.0° C. |
| 95% | 336.5° C. |
| Final point | 349.0° C. |

The results are summarized in Table 2 and show the effectiveness of the products that are obtained according to the invention.

TABLE 2

Results of the Clogging of Injectors (XUD9 - 6 hours)

| Length of stroke of the needle (mm) | 0.1 | 0.2 | 0.3 |
|---|---|---|---|
| Average residual flow (%) | | | |
| Gas oil (reference) | 3.7 | 28.4 | 50.0 |
| Gas oil + 500 ppm of additive of Example 1 | 45.2 | 60.3 | 69.1 |
| Gas oil + 500 ppm of additive of Example 2 | 49.0 | 65.2 | 73.6 |
| Gas oil + 500 ppm of additive of Example 3 | 59.7 | 74.3 | 79.9 |

EXAMPLE 8

Test on a Gasoline Engine

Formulations with a base of the additive of Example 1 and polypropylene glycol of a molecular weight that is close to 1000 that are already used during syntheses are prepared. Engine tests are conducted to evaluate the influence of additives on the amounts of deposits at the intake valves.

The test procedure uses a Mercedes M 102 E engine, and it runs in a cyclic manner according to a door-to-door diagram for 60 hours. The reference fuel that is used is an unleaded fuel that has a "research" octane number of 96.8 and whose characteristics are presented in detail in Table 3.

The tests are conducted in the presence of various concentrations of additive and polypropylene glycol and compared to a test with no additive. The results that are obtained (Table 4) are expressed by weight (grams) of deposits on the annular intake valves. They show the effectiveness of the additives that are obtained according to the invention.

TABLE 3

| Density at 15° C. | 754.0 kg/m³ |
|---|---|
| Reid vapor pressure | 618 hPa |
| Distillation | |
| Initial pint | 30.7° C. |
| 5% | 45.0° C. |
| 10% | 51.5° C. |
| 20% | 65.5° C. |
| 30% | 80.5° C. |
| 40% | 97.0° C. |
| 50% | 111.0° C. |
| 60% | 123.0° C. |
| 70% | 138.0° C. |
| 80% | 154.5° C. |
| 90% | 172.8° C. |
| 95% | 185.0° C. |
| Final point | 205.0° C. |

TABLE 4

Test M 102 E - Amounts of Deposit (in Grams)

| Additive of Example 1 (ppm) | PPG (ppm) | Valve No. 1 | Valve No. 2 | Valve No. 3 | Valve No. 4 | Total | Average deposit/valve |
|---|---|---|---|---|---|---|---|
| 0 | 0 | 0.278 | 0.479 | 0.186 | 0.188 | 1.131 | 0.283 |
| 130 | 200 | 0.005 | 0.011 | 0.043 | 0.001 | 0.060 | 0.015 |
| 400 | 0 | 0.036 | 0.002 | 0.038 | 0.034 | 0.110 | 0.028 |
| 400 | 174 | 0.014 | 0.005 | 0.001 | 0.015 | 0.035 | 0.009 |

What is claimed:

1. A simplified process for preparation of an alkenylsuccinimide or a polyalkenylsuccinimide, comprising a stage (a) in which an alkenylsuccinic anhydride or a polyalkenylsuccinic anhydride is prepared by bringing about an ene-synthesis reaction between at least one olefin or one polyolefin and at least one unsaturated dicarboxylic anhydride that is unsubstituted maleic anhydride or a maleic anhydride substituted by 1 or 2 methyl groups, characterized in that said reaction is toluene or xylene at a ratio of between 30 and 70% by weight relative to the reaction mixture, in which a fraction of said unsaturated dicarboxylic anhydride does not react with said olefin or polyolefin; a stage (b) in which the resultant product of stage (a) that contains unsaturated, unreacted dicarboxylic anhydride is reacted with at least one alcohol or an amine to form a soluble moiety; and a stage (c) in which the resultant product that is obtained in stage (b) is reacted with an amine having a higher activity than the soluble moiety produced in step (b), so as to form said alkenylsuccinimide or polyalkenylsuccinimide.

2. A process according to claim 1, wherein said olefin or polyolefin has an average molecular weight that is between 400 and 10,000 in number.

3. A process according to claim 1, wherein said polyolefin is a polyisobutene having an "exo" double bond content that is greater than 50%.

4. A process according to claim 1, wherein the proportion of aromatic solvent used in stage (a) is 35 to 60% by weight relative to the reaction mixture.

5. A process according to claim 1, wherein the reaction of stage (a) is carried out at a temperature of 150° to 300° C.

6. A process according to claim 1, wherein the maleic anhydride or substituted maleic anhydride is used in stage (a) at a molar ratio of 0.5:1 to 2.1 with the olefin or the polyolefin.

7. A process according to claim 1, wherein in stage (b), any alcohol employed is at least a propylene glycol, a copolymer of ethylene oxide and propylene oxide, or a polypropylene glycol monoether and any amine employed is at least a polyoxyalkylene-amine, an alkenylamine, or a polyalkenylsuccinimide with a primary amine group.

8. A process according to claim 1, wherein in stage (b), the alcohol or the amine is used at a molar ratio of 1 to 1.5 relative to the maleic anhydride or the residual substituted maleic anhydride.

9. A process according to claim 1, wherein in stage (b), the reaction temperature ambient temperature to the boiling point of the solvent.

10. A process according to claim 7, wherein in stage (c), the amine is a polyethylene-polyamine that is selected from the group consisting of triethylenetetramine and tetraethylenepentamine.

11. A process according to claim 10, wherein the polyethylene-polyamine is used at a molar ratio of 0.5 to 1 relative to the alkenylsuccinic anhydride or polyalkenylsuccinic anhydride formed in stage (a).

12. A process according to claim 11, wherein in stage (c), the reaction is carried out at the boiling point of the solvent.

13. A composition obtained by a process according to claim 1.

14. A liquid hydrocarbon fuel containing a composition according to claim 13 as a detergent additive.

15. A formulation of additives for fuels comprising a composition according to claim 13 and a polypropylene glycol or a polypropylene glycol ether.

16. A lubricant containing a composition according to claim 13 as an ashless dispersing additive.

17. In a process for preparing an alkenylsuccinic anhydride or a polyalkenylsuccinic anhydride comprising reacting at least one olefin or polyolefin with unsubstituted maleic anhydride or or maleic anhydride substituted by 1 or 2 methyl groups, the improvement comprising conducting the reaction in toluene or xylene at a proportion of between 30 and 70% by weight relative to the reaction mixture.

18. A process according to claim 17, wherein the proportion is 35% to 60% by weight.

* * * * *

UNITED STATES PATENT AND TRADEMARK OFFICE
CERTIFICATE OF CORRECTION

PATENT NO. : 5,735,915
DATED : April 7, 1998
INVENTOR(S) : GATEAU et al.

It is certified that error appears in the above-identified patent and that said Letters Patent is hereby corrected as shown below:

Claim 6, line 3:  change "2.1" to -- 2:1 --.

Claim 8, line 2:  change "1 to 1.5" to -- 1:1 to 1.5:1 --.

Claim 11, line 2: change "0.5 to 1" to -- 0.5:1 to 1:1 --.

Signed and Sealed this

Twenty-first Day of July, 1998

Attest:

Attesting Officer

BRUCE LEHMAN

Commissioner of Patents and Trademarks